United States Patent [19]

Schultz et al.

[11] 4,178,316
[45] Dec. 11, 1979

[54] METHOD OF PREPARING 1,1-DIFLUOROETHYLENE FROM ACETYLENE

[75] Inventors: Neithart Schultz; Peter Martens, both of Rheinfelden; Hans-Joachim Vahlensieck, Wehr, all of Fed. Rep. of Germany

[73] Assignee: Dynamit Nobel Aktiengesellschaft, Troisdorf, Fed. Rep. of Germany

[21] Appl. No.: 856,567

[22] Filed: Dec. 1, 1977

Related U.S. Application Data

[63] Continuation-in-part of Ser. No. 800,605, May 25, 1977.

[30] Foreign Application Priority Data

Dec. 31, 1976 [DE] Fed. Rep. of Germany ....... 2659712

[51] Int. Cl.² .............................................. C07C 17/34
[52] U.S. Cl. ............................. 260/653.5; 204/163 R; 252/464; 260/653.6
[58] Field of Search .................... 204/163 R; 252/464; 260/653.5, 653.6

[56] References Cited

U.S. PATENT DOCUMENTS

| 2,644,845 | 7/1953 | McBee ............................ 204/163 R |
| 3,073,871 | 1/1963 | Snavely et al. ................... 260/653.6 |
| 3,187,060 | 6/1965 | Petit et al. ...................... 260/653.6 X |
| 3,697,443 | 10/1972 | Shinoda et al. ............... 260/653.6 X |
| 3,720,722 | 3/1973 | Wada et al. ................... 260/653.6 X |
| 4,053,529 | 10/1977 | Martens ............................. 260/653.5 |

FOREIGN PATENT DOCUMENTS

| 1261501 | 1/1972 | United Kingdom . |
| 1309361 | 3/1973 | United Kingdom . |
| 380631 | 8/1973 | U.S.S.R. ............................... 260/653.5 |

*Primary Examiner*—Leland A. Sebastian
*Attorney, Agent, or Firm*—Sprung, Felfe, Horn, Lynch & Kramer

[57] ABSTRACT

An improvement in a method of preparing 1,1-difluoroethylene from 1,1-difluoroethane by photochlorinating 1,1-difluoroethane to 1,1-difluoro-1-chloroethane and immediately thereafter reacting the reaction products of the photochlorination at a temperature between 550 and 750° C. without isolation of the 1,1-difluoro-1-chloroethane, the improvement residing in employing as the difluoroethane charge an unrefined product of the hydrofluorination of acetylene which unrefined reaction product contains up to 3 volume percent acetylene and a maximum of 8 volume percent vinyl fluoride, especially a unrefined reaction product in which the difluoroethane has not been isolated.

5 Claims, No Drawings

METHOD OF PREPARING 1,1-DIFLUOROETHYLENE FROM ACETYLENE

CROSS REFERENCE TO PATENT APPLICATION

This is a continuation-in-part of copending application Ser. No. 800,605 filed May 25, 1977 for "Method Of Preparing 1,1-Difluoroethylene."

BACKGROUND OF THE INVENTION

1. Field Of The Invention

The subject matter of the present invention is a method of preparing 1,1-difluoroethylene in which acetylene is used as the starting product, and in which no intermediate products are isolated.

2. Discussion Of The Prior Art

The preparation of 1,1-difluoroethylene is, as it is known, performed in three steps: in the first step, 1,1-difluoroethane is obtained by the hydrofluorination of acetylene. Thereafter, the purified 1,1-difluoroethane is chlorinated to form 1,1-difluoro-1-chloroethane which is isolated from the chlorination products. In a third step, hydrogen chloride is split off thermally from the 1,1-difluoro-1-chloroethane with the formation of 1,1-difluoroethylene.

It is known to hydrofluorinate acetylene in the presence of a catalyst consisting of a tableted mixture of aluminum fluoride and bismuth fluoride. By means of this catalyst no more than 97% of the acetylene can be reacted. The reaction products contain 70 to 72 wt.-% of 1,1-difluoroethane and 25 to 27 wt.-% of vinyl fluoride. Prior to the further processing of a product contained in such a mixture, the mixture must be refined by distillation before using the 1,1-difluoroethane in further reactions.

As a catalyst for the hydrofluorination of acetylene to 1,1-difluoroethane, a catalyst containing aluminum fluoride has been proposed which is prepared by imbibing γ- or η-aluminum oxide with a bismuth salt and manganese salt solution, drying the aluminum oxide impregnated with the salts at temperatures up to 100° C., and then heating it, at first in a nitrogen atmosphere, and later in air with increasing concentrations of hydrogen fluoride up to a 100% hydrogen fluoride atmosphere, at temperatures between 150° and 250° C. The preparation of such a catalyst has been described, for example, in German Offenlegungsschrift No. 20 00 200. The reaction product obtained by hydrofluorination with such a catalyst can contain up to 2% of acetylene and a maximum of about 4.5% of vinyl fluoride. Consequently, both of the by-products have hitherto always been separated prior to any further processing of the difluoroethane.

The further processing of a purified 1,1-difluoroethane to 1,1-difluoroethylene in a one-step process has already been described in U.S. Ser. No. 800,605, assigned to the assignee hereof, the disclosure of which is hereby incorporated herein by reference. In the method described in this application, 1,1-difluoroethane is photochlorinated to 1,1-difluoro-1-chloroethane and immediately thereafter the reaction products obtained are heated at temperatures between 550° and 750° C. without isolation of the 1,1-difluoro-1-chloroethane.

SUMMARY OF THE INVENTION

In further development of this method it has now been found that an unrefined reaction product of the catalytic hydrofluorination of acetylene containing up to 3% by volume of acetylene and a maximum of 8.0% by volume of vinyl fluoride can be used as a starting product for this process.

In spite of the acetylene and vinyl fluoride impurities in the starting product, the use of this method results in yields of 1,1-difluoroethylene in excess of 90% with respect to the acetylene charged. The by-products present, especially the unreacted acetylene, therefore virtually do not interfere with the overall reaction. This is surprising in that it is as yet unknown to photochlorinate acetylene-containing gas mixtures without problems.

In the method of the invention, the advantage is obtained over the known methods in which the intermediate products are isolated that a large amount of equipment can be dispensed with. Distillation apparatus, and storage and transportation tanks required in a technical scale plant by the known processes are unnecessary.

In a first process step, acetylene is hydrofluorinated with the aid of a hydrofluorination catalyst. An especially good catalyst has proven to be one which is prepared by imbibing γ- or η-aluminum oxide with the solution of bismuth salts, together with manganese salts if desired, then heating to temperatures between 150° and 250° C., at first in a nitrogen atmosphere and then, after complete drying, in a mixture of air and increasing concentrations of hydrogen fluoride until the atmosphere consists of 100% hydrogen fluoride.

If the aluminum oxide has been impregnated with only a bismuth salt solution, the finished catalyst will contain from 0.1 to 20% by weight of bismuth, 35 to 66 wt.-% of fluorine, and 24 to 42 wt.-% of aluminum, and the balance will consist mostly of oxygen. If a manganese salt solution is additionally used for the impregnation, the finished catalyst will then contain an additional 0.1 to 10% of manganese, while the aluminum content will diminish to 20 to 38 wt.-% and the fluorine content to 32 to 60 wt.-%.

The preparation of the catalyst is performed as follows:

γ- or η-aluminum oxide, preferably heated at 80° C. in a vacuum of less than 1 Torr for about one hour, is imbibed with the aqueous solution of a bismuth salt and a manganese salt. Suitable bismuth salts are water-soluble or acid-soluble bismuth salts whose solution is stabilized, if necessary, with a complexing agent. This complexing agent makes it possible, in the case of poorly soluble bismuth salts, and also manganese salts, to prepare a homogeneous solution of these salts. Examples of suitable complexing agents are hydroxyl-group-containing organic compounds from among the sugar alcohols, such as, for example, mannitol, sorbitol or ribitol, or hydroxy acids, such as, for example, tartaric acid, lactic acid, or the sugar acids. Amines and nitriles are also suitable as complexing agents, examples being ethylene diamine, nitrilotriacetic acid or succinodinitrile.

A homogeneous solution can also be obtained by the establishment of a suitable acid pH value.

Suitable bismuth salts are water-soluble or acid-soluble bismuth salts whose solution is stabilized, if necessary, by the above-mentioned complexing agents.

Preferably, use is made of the bismuth salts or bismuth oxysalts of nitric acid, sulfuric acid, hydrochloric acid or perchloric acid.

The concentration of the bismuth salt solution is not essential to the method. It is selected in accordance with the desired bismuth content of the catalyst.

It is preferable to use as the manganese compound the salt having the same anion as the bismuth salt that is used. Any other water-soluble or acid-soluble manganese salt can be used, however, provided that, under the stated conditions, it does not form an insoluble precipitate with the bismuth salt that is used.

Preferably, the manganese(II) and bismuth salts or bismuth oxysalts of nitric acid, sulfuric acid, hydrochloric acid or perchloric acid are used.

The concentration of the manganese salt solution is also not essential to the method. It is selected in accordance with the desired metal content of the catalyst.

The aluminum oxide imbibed with the bismuth salt or bismuth and manganese salt solution is then dried at temperatures up to 100° C. and immediately thereafter it is heated in a nitrogen atmosphere to 150° to 250° C. After the catalyst has been completely dried, the nitrogen is replaced by air and increasing concentrations of hydrogen fluoride. The exothermic reaction that then takes place is also performed at temperatures between 150° and 250° C. Towards the end of the exothermic reaction, the catalyst is heated in a 100% hydrogen fluoride atmosphere until the exothermic reaction ceases.

For the performance of the hydrofluorination reaction, acetylene is mixed with the later-mentioned excess of hydrogen fluoride and preheated to the necessary reaction temperature. The preheated mixture is passed through the catalyst which is held constantly at a temperature between 150° and 350° C. The catalyst in this case can be disposed in either a solid bed or in a fluid bed.

After passing through the catalyst, the gas mixture is washed in a known manner, partially dried, and then fed directly to the photochlorination without separation of the impurities. It is also possible, however, to store this gas mixture temporarily in a gasometer and then photochlorinate it directly.

By using this method, yields of 96 to 98% of the desired 1,1-difluoroethane are obtained, the acetylene transformation being virtually complete. This high transformation of acetylene is obtained at a detention time of as little as 5 to 30 seconds. The preferred detention time is between 5 and 45 seconds.

The preferred temperature range is between 200° and 280° C. The higher the temperature that is selected is, the shorter the detention time can be made, with virtually the same transformations and yields.

In contrast to other methods, the hydrofluorination of acetylene does not need to be performed with an excess of hydrofluoric acid above the stoichiometrically necessary amount of 2 moles of HF per mole of acetylene. EVen in the case of a stoichiometric ratio between the reactants, it takes place in a virtually quantitative manner. It is recommendable to use an excess of approximately 5% of hydrofluoric acid. Basically, it is also possible to use an excess of as much as 50% of hydrofluoric acid.

The preparation of the difluorethane, however, can be performed also by hydrofluorinating acetylene with the aid of a different catalyst, if in that case a gas mixture forms which contains not more than 3 vol.-%, preferably not more than 2 vol.-%, of acetylene. The vinyl fluoride content in the mixture can amount to up to 8 vol.-%, preferably up to 7 vol.-%. In these cases, too, the gas mixture that forms in the hydrofluorination can be subjected directly to the chlorination reaction without separation of the acetylene or other reaction products.

For the achievement of particularly high transformations as well as yields, it is recommendable to use two similar reactors, filled with the same catalyst, in tandem, the second one having a temperature approximately 20° to 50° C. lower than the first. This brings it about that, when the gas mixture emerging from the first reactor after a virtually quantitative transformation, has passed through the second reactor, the vinyl fluoride, which is its predominant by-product, is also largely transformed to difluoroethane by reacting with the excess hydrogen fluoride that is present.

The gas mixture that can be used for the photochlorination in accordance with U.S. Ser. No. 800,605 can contain the most important by-products, acetylene and vinyl fluoride, which occur in the catalytic hydrofluorination of acetylene, in amounts of up to 3 vol.-% and 8 vol.-%, respectively. The preferentially tolerable maximum limit for the vinyl fluoride content is 7% by volume. Other by-products which occur in the catalytic hydrofluorination of acetylene can also be present in small amounts in the gas mixture that is to be chlorinated.

The chlorination of the mixture of 1,1-difluoroethane, acetylene and vinyl fluoride is performed in a manner that is known in itself. It is performed preferably in the presence of light, the wavelength of the light rays being able to be both in the visible range and in the ultraviolet range. The preferred range is between 500 and 600 nm.

The molar ratio between the hydrofluorination product and the chlorine during the chlorination is to be 1:1. A slight excess of chlorine is possible. However, the said molar ratio should not exceed 1:1.2, insofar as possible.

The chlorination is performed at temperatures between 0° and 150° C. The preferred temperature range is between 20° and 70° C. The detention times in the chlorination reactor, which consists preferably of glass, is to be, insofar as possible, between 20 and 100 seconds, with respect to 0° C. and the empty reactor.

Immediately following the chlorination, the chlorination products are subjected to dehydrochlorination by pyrolysis. They consist mainly of 1,1-difluoro-1-chloroethane and hydrogen chloride, plus small amounts of more highly chlorinated fluorochloroethanes and unreacted difluoroethane. The content of the higher-boiling by-products is generally between 2 and 4% by volume.

The dehydrochlorination is performed at temperatures between 500° and 750° C. The reaction products that form in the chlorination of 1,1-difluoroethane, mainly the liberated hydrogen chloride, enable the pyrolysis of the 1,1-difluoro-1-chloroethane to the desired 1,1-difluoroethylene to provide a virtually 100% yield. These high yields are obtained especially when the dehydrochlorination reactor is filled with a material of good thermal conductivity. Suitable as such are, for example, metal chips which are not attacked under the conditions of the reaction, such as nickel chips, for example. The preferred pyrolysis temperature is between 600° and 720° C.

The detention time in the pyrolysis reactor is to be between 1 and 150 seconds, with respect to the empty reactor and 0° C. The preferred range is between 2.5 and 90 seconds.

The reactor must be made of a material which is not attacked under the reaction conditions. Nickel reactors, in the form of tube reactors, are especially suitable.

In general, the dehydrochlorination is performed at atmospheric pressure or at the pressure which establishes itself in the course of the reaction. This pressure is generally not higher than about 1.1 atmospheres. Basically, however, it is also possible to operate at higher pressures.

The method of the invention is practiced preferably continuously. In this case, the hydrofluorination reactor, chlorination reactor and dehydrochlorination reactor are connected directly in series in that order. Between the hydrofluorination reactor and the chlorination reactor it is desirable to interpose a water washing for the removal of excess hydrogen fluoride. The reaction products, after leaving the last reactor, are washed with water and/or dilute alkali hydroxide solution and then dried. The gas mixture obtained then contains as impurities mainly more highly chlorinated products, which are easy to separate in a known manner from the 1,1-difluoroethylene. The yields of 1,1-difluoroethylene are then better than 90% with respect to the acetylene charged.

EXAMPLES

EXAMPLE 1

For the preparation of the catalyst, 700 g of γ-aluminum oxide in pellets of 3 mm diameter are subjected to a vacuum of less than 1 Torr for one hour at 80° C. in a glass tube provided with a heating jacket. Then the temperature is reduced in vacuo to room temperature, and a solution of 160 g of $Bi(NO_3)_3.5H_2O$, 65 g of $Mn(NO_3)_2 \cdot 4H_2O$ and 80 ml of 14 N nitric acid in 900 ml of $H_2O$ is allowed to flow into the tube. After the imbibing mixture has been exposed to air it is let stand for one hour at 80° C. Then the aqueous phase is withdrawn and the catalyst composition is given a preliminary drying in vacuo, using a water jet pump.

For the hydrofluorination, the catalyst is placed in a jacketed nickel tube 150 cm long and 5 cm in diameter, the temperature of which can be regulated by means of circulating oil. At 200° C., the catalyst is thoroughly dried with nitrogen, and then activated with a mixture of air and an increasing concentration of hydrogen fluoride. By varying the HF concentration the temperature is kept always below 250° C. After a 100% hydrogen fluoride current is reached, the treatment is continued for another hour, and then drying is performed for one hour with air. The bismuth content of the catalyst then amounts to about 5%, the manganese content content to about 3% and the fluoride content is around 50%.

A gaseous mixture of 12.6 moles per hour of hydrogen fluoride and 6 moles per hour of acetylene (molar ratio 2.1:1) is passed through the catalyst, activated as described above, in a nickel reactor having a heated capacity of 1.8 liters, at 230° to 240° C.

After passing through a water washing, the reaction mixture is mixed with 6.6 moles per hour of chlorine and subjected to the gaseous phase reaction at about 30° C. in a 3.6-liter glass reactor under irradiation from a 250 Watt Osram Power Star HQJ halogen metal vapor lamp.

The mixture leaving the chlorination reactor is carried directly into a nickel reactor of a heated capacity of 0.75 liter, heated to approximately 690° C. The reaction product emerging from the reactor is washed with water and dilute caustic soda solution and dried.

A mixture of organic compounds is obtained having the following composition determined by gas chromatography:

| | |
|---|---|
| $CF_2=CH_2$ | 91.9% |
| $CHF_2—CH_3$ | 0.5% |
| $CF_2Cl—CH_3$ | 0.2% |
| $CF_2=CHCl$ | 1.4% |
| Higher boiling compounds | 6.0% |

With a 100% transformation of the acetylene charged, the three-step overall reaction thus took place with a 91.9% yield.

The manner in which the experimental apparatus is set allows one to take samples, freed of halogen hydrides and chlorine by water washing, from the output of each reactor, so as to permit checking the individual steps of the reaction. In this manner, the following partial results were determined by gas chromatographic analysis:

(a) Hydrofluorination (Step 1):

| | |
|---|---|
| $CHF_2—CH_3$ | 97.4% |
| $CHF=CH_2$ | 2.5% |
| $CH≡CH$ | 0.1% |

Corresponding to a 99.9% transformation; 97.5% yield.

(b) Chlorination (Step 2):

| | |
|---|---|
| $CF_2Cl—CH_3$ | 94.1% |
| $CHF_2—CH_3$ | 2.3% |
| Higher boiling substances | 3.6% | which, in consideration of the previously stated composition of the starting mixture subjected to the chlorination, corresponds to a yield of 98.9% at a 97.6% transformation.

(c) Thermal Cleavage (Step 3):

The above-stated result, which is identical as regards the product composition to the overall result, corresponds to a yield of 97.9% at a 99.8% transformation, also with respect to the composition of the starting mixture specified under (b).

EXAMPLE 2

The experiment on which this example is based was performed in the apparatus described in Example 1. In order to achieve the completest possible transformation of acetylene to difluorethane, a second reactor filled with the same catalyst was connected to the hydrofluorination reactor used in the hydrofluorination (Step 1), in which the temperature was maintained at about 200° C., i.e., about 30° to 40° lower than in the first reactor.

OVERALL RESULTS

Under otherwise similar conditions, the following overall result was obtained:

| | |
|---|---|
| $CF_2=CH_2$ | 93.7% |
| $CHF_2—CH_3$ | 1.8% |
| $CF_2Cl—CH_3$ | 0.2% |
| $CF_2=CHCl$ | 1.1% |

| -continued | |
|---|---|
| Higher boiling substances | 3.3% |

The overall reaction resulted in a 93.7% yield of 1,1-difluorethylene for a 100% transformation of the acetylene input.

An analysis in accordance with Example 1 yielded the following partial results:

(a) Hydrofluorination:

| $CHF_2$—$CH_3$ | 99.0% |
|---|---|
| $CHF$=$CH_2$ | 0.5% |
| $CH$≡$CH$ | 0.5% |

99.5% transformation, 99.5% yield.

(b) Chlorination:

| $CF_2Cl$—$CH_3$ | 95.8% |
|---|---|
| $CHF_2$—$CH_3$ | 2.0% |
| Higher boiling components | 2.2% |

98.0% transformation, 98.8% yield.

(c) Cleavage:

Gas chromatographically determined composition (see above under "Overall Results")
99.8% transformation, 98.0% yield.

EXAMPLE 3

In order to demonstrate the efficiency of the overall reaction, an experiment was selected in which the hydrofluorination catalyst had a decidedly reduced activity due to long use and was in need of regeneration. The experimental arrangement and performance were the same as in Example 1, i.e., only one hydrofluorination reactor was again used, in order to intentionally produce a relatively high content of $CHF$=$CH_2$ in the raw product of partial reaction 1.

Overall result:

| $CF_2$=$CH_2$ | 90.0% |
|---|---|
| $CHF_2$—$CH_3$ | 1.1% |
| $CF_2Cl$—$CH_3$ | 0.1% |
| $CF_2$=$CHCl$ | 2.1% |
| Higher boiling substances | 6.8% |

Overall transformation 100%, overall yield 90.0%.

The breakdown into the individual steps of the reaction was as follows:

(a) Hydrofluorination:

| $CHF_2$—$CH_3$ | 94.9% |
|---|---|
| $CHF$=$CH_2$ | 4.2% |
| $CH$≡$CH$ | 1.0% |

99.0% transformation, 95.8% yield.

(b) Chlorination:

| $CF_2Cl$—$CH_3$ | 92.2% |
|---|---|
| $CHF_2CH_3$ | 2.4% |
| Higher boiling substances | 5.4% |

97.5% transformation, 99.6% yield.

(c) Cleavage:

Product composition: see above.
99.9% transformation, 97.7% yield.

What we claim is:

1. In a process for preparing 1,1-difluoroethylene by subjecting 1,1-difluoroethane to photochlorination at 20° to 150° C. to form 1,1-difluoro-1-chloroethane and effecting pyrolysis thereof without isolation of said 1,1-difluoro-1-chloroethane, the improvement which comprises employing as the difluoroethane charge an acetylene containing unrefined reaction product obtained by the catalytic hydrofluorination of acetylene employing an acetylene:HF mol ratio of 1:2.0–2.1 at a temperature up to 350° C. and a contact time of 5–30 seconds, said unrefined reaction product containing up to 3 volume percent acetylene and a maximum of 8 volume percent vinyl fluoride.

2. A process according to claim 1 wherein said unrefined reaction product is one in which the 1,1-difluoroethane has not been isolated.

3. A process according to claim 1 wherein the difluoroethane unrefined reaction product charged is one prepared by hydrofluorinating acetylene employing a catalyst which has been produced by:
   (a) imbibing γ- or η-aluminum oxide with a homogeneous solution of a bismuth salt;
   (b) drying said aluminum oxide imbibed with said bismuth salt solution at a temperature of up to 100° C; and
   (c) heating said dried aluminum oxide in a nitrogen atmosphere until it completely dries and then replacing the nitrogen with air and increasing the concentration of hydrogen fluoride up to a 100% hydrogen fluoride atmosphere until the cessation of the exothermic reaction ensues, the processing being carried out at a temperature between 150° and 250° C., the finished catalyst consisting of:
   0.1 to 20 weight percent bismuth
   35 to 66 weight percent fluorine
   24 to 42 weight percent aluminum and the balance, if any, oxygen.

4. A process according to claim 3 wherein in the preparation of the catalyst the aluminum oxide is additionally imbibed with a manganese salt solution in step (a) and the finished catalyst consists essentially of:
   0.1 to 20 weight percent bismuth
   0.1 to 10 weight percent manganese
   32 to 60 weight percent fluorine
   20 to 38 weight percent aluminum, the balance, of any, oxygen.

5. A process according to claim 1 wherein the unrefined reaction product containing the difluoroethane contains not more than 2 volume percent acetylene and not more than 7 volume percent vinyl fluoride.

* * * * *